(12) United States Patent
Strange et al.

(10) Patent No.: US 11,577,243 B2
(45) Date of Patent: *Feb. 14, 2023

(54) MULTIPLE-USE SENSOR ASSEMBLY FOR BODY FLUIDS

(71) Applicant: Radiometer Medical ApS, Brønshøj (DK)

(72) Inventors: Christian Strange, Skibby (DK); Peter Frischauf, Brøndby (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 56 days.

This patent is subject to a terminal disclaimer.

(21) Appl. No.: 17/355,492

(22) Filed: Jun. 23, 2021

(65) Prior Publication Data

US 2021/0316307 A1  Oct. 14, 2021

Related U.S. Application Data

(63) Continuation of application No. 16/472,300, filed as application No. PCT/EP2017/083300 on Dec. 18, 2017, now Pat. No. 11,071,980.

(30) Foreign Application Priority Data

Dec. 23, 2016 (DK) .......................... PA 2016 00790

(51) Int. Cl.
*B01L 3/00* (2006.01)
*G01N 33/487* (2006.01)

(52) U.S. Cl.
CPC .. *B01L 3/502746* (2013.01); *G01N 33/48707* (2013.01); *B01L 2300/0627* (2013.01); *B01L 2400/086* (2013.01)

(58) Field of Classification Search
CPC ............ G01N 33/48707; G01N 33/492; B01L 2300/0627; B01L 2300/0663;
(Continued)

(56) References Cited

U.S. PATENT DOCUMENTS 4,734,184 A  3/1988  Burleigh et al.
4,871,439 A  10/1989  Enzer et al.
(Continued)

FOREIGN PATENT DOCUMENTS

CN   101687191 A   3/2010
CN   106081069 A   11/2016
(Continued)

OTHER PUBLICATIONS

English translation of DE20202056U1, applicant: Gerätebau (Year: 2002).*

(Continued)

*Primary Examiner* — Jennifer Wecker
*Assistant Examiner* — Jonathan Bortoli
(74) *Attorney, Agent, or Firm* — Finnegan, Henderson, Farabow, Garrett & Dunner, LLP

(57) ABSTRACT

The present invention relates to a sensor assembly (1) for body fluids. The sensor assembly (1) comprises: a measurement chamber (2) extending in an axial direction from an inlet end (3) to an outlet end (4), the measurement chamber having a transverse cross-section with side walls (5, 6) defining a chamber width in a horizontal direction, and with top and bottom walls (8, 7) defining a chamber height in a vertical direction, each of the side walls (5, 6), top wall (8) and bottom wall (7) having a respective wall wettability for aqueous solutions; a first sensor (10a-h) adapted to measure a first parameter of body fluids, the first sensor (10 a-h) having a first sensor surface (11a-h) exposed to the inside of the measurement chamber at a first axial position, the first
(Continued)

sensor surface (11*a-h*) having a first wettability for aqueous solutions; and a second sensor (20) adapted to measure a second parameter of body fluids, the second sensor (20) having a second sensor surface (21) exposed to the inside of the measurement chamber (2) at a second axial position upstream or downstream from the first axial position, the second sensor surface (21) having a second wettability for aqueous solutions higher than the first wettability. At the second axial position, the chamber width exceeds the width of the second sensor surface (21), and the measurement chamber has a widening (22) in a horizontal direction as compared to the first axial position.

20 Claims, 3 Drawing Sheets

(58) Field of Classification Search
CPC ....... B01L 2300/0858; B01L 2300/161; B01L 2400/086; B01L 3/502; B01L 3/502746; H01L 2224/32225; H01L 2224/48091; H01L 2224/48227; H01L 2224/48465; H01L 2224/73265; H01L 24/29; H01L 24/32; H01L 2924/351
See application file for complete search history.

(56) References Cited

U.S. PATENT DOCUMENTS

| | | | |
|---|---|---|---|
| 5,228,350 | A | 7/1993 | Karpf et al. |
| 6,037,178 | A | 3/2000 | Leiner et al. |
| 11,197,618 | B2 | 12/2021 | Edelman et al. |
| 2004/0028566 | A1 | 2/2004 | Ko et al. |
| 2004/0256227 | A1 | 12/2004 | Shin et al. |
| 2005/0114062 | A1 | 5/2005 | Davies et al. |
| 2009/0060789 | A1 | 3/2009 | Aas et al. |
| 2009/0321258 | A1 | 12/2009 | Abel et al. |
| 2013/0136657 | A1* | 5/2013 | Hofmann .......... B01L 3/502707 422/68.1 |
| 2016/0116427 | A1 | 4/2016 | Laurenson |
| 2016/0169867 | A1 | 6/2016 | Khine et al. |

FOREIGN PATENT DOCUMENTS

| | | | |
|---|---|---|---|
| DE | 202 02 056 U1 | 7/2002 | |
| DE | 20202056 U1 * | 7/2002 | ......... G01N 27/3272 |
| EP | 0 754 944 A1 | 1/1997 | |
| EP | 1 753 872 B1 | 2/2007 | |
| EP | 2 811 299 A1 | 12/2014 | |
| JP | H08500679 A | 1/1996 | |
| JP | 9-33537 | 2/1997 | |
| JP | 2004-279150 A | 10/2004 | |
| JP | 2004-354388 | 12/2004 | |
| JP | 2006-266795 | 10/2006 | |
| JP | 2007-514928 | 6/2007 | |
| JP | 2008-256725 A | 10/2008 | |
| JP | 2010-525338 | 7/2010 | |
| JP | 2018-036091 | 3/2018 | |
| JP | 2019-532700 A | 11/2019 | |
| KR | 10-2224729 | 3/2021 | |
| WO | WO 2005/103669 A1 | 11/2005 | |
| WO | WO 2007/021755 A2 | 2/2007 | |
| WO | WO 2012/081695 A1 | 6/2012 | |
| WO | WO 2016/142067 A1 | 9/2016 | |

OTHER PUBLICATIONS

International Search Report for International Application No. PCT/EP2017/083300, dated Feb. 28, 2018.

Written Opinion of the International Search Authority of International Application No. PCT/EP2017/083300.

* cited by examiner

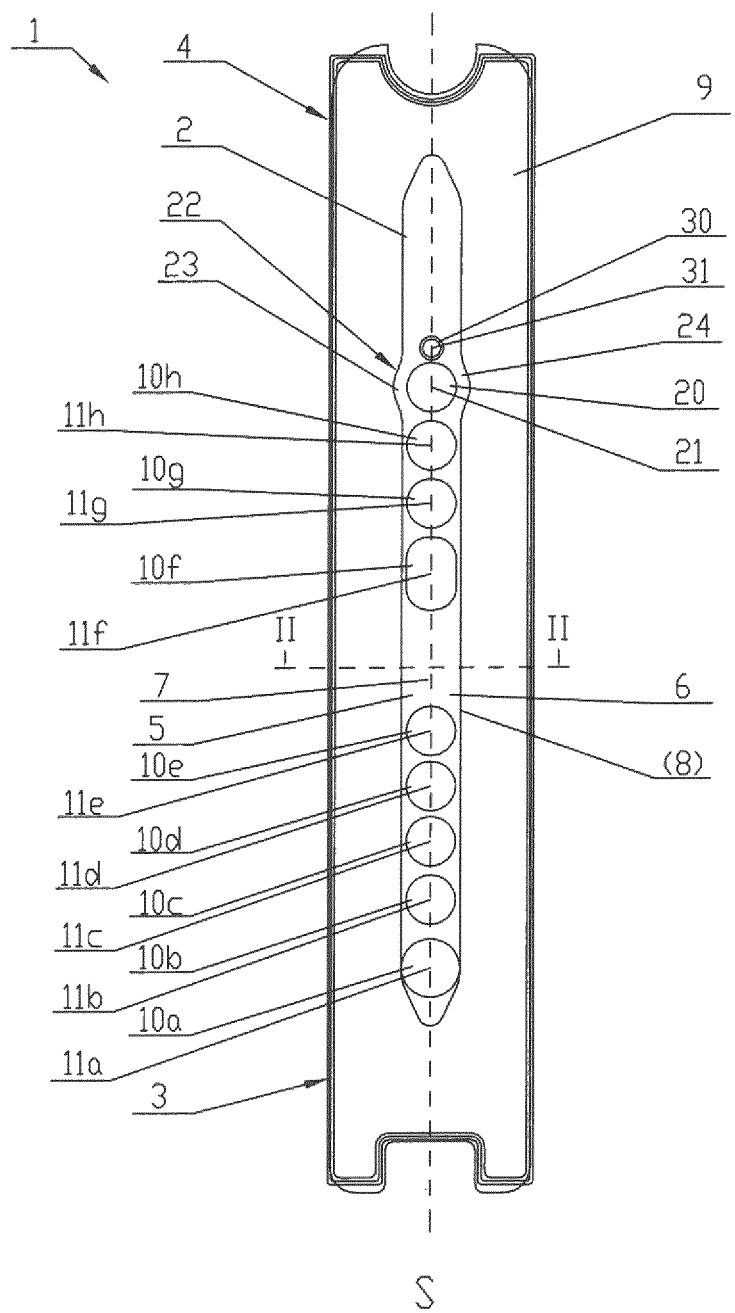
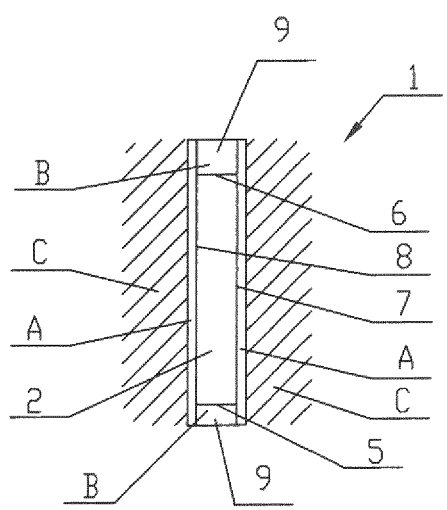
Fig. 1
Fig. 2

MULTIPLE-USE SENSOR ASSEMBLY FOR BODY FLUIDS

This application is a continuation of U.S. patent application Ser. No. 16/472,300, filed Jun. 21, 2019, which is a national stage filing under 35 U.S.C. § 371 of International Application No. PCT/EP2017/083300, filed on Dec. 18, 2017, which claims priority of Danish Patent Application No. PA 2016 00790, filed Dec. 23, 2016. The contents of these applications are each incorporated herein by reference in their entirety.

The present invention relates to a sensor assembly for bio-analytic measurements in body fluids. The sensor assembly comprises: a measurement chamber extending in an axial direction from an inlet to an outlet, the measurement chamber having a transverse cross-section with side walls defining a chamber width in a horizontal direction, and with top and bottom walls defining a chamber height in a vertical direction, each of the side walls, top wall and bottom wall having a respective wall wettability for aqueous solutions; a first sensor adapted to measure a first parameter of body fluids, the first sensor having a first sensor surface exposed to the inside of the measurement chamber at a first axial position, the first sensor surface having a first wettability for aqueous solutions; and a second sensor adapted to measure a second parameter of body fluids, the second sensor having a second sensor surface exposed to the inside of the measurement chamber at a second axial position upstream or downstream from the first axial position, the second sensor surface having a second wettability for aqueous solutions higher than the first wettability.

BACKGROUND OF THE INVENTION

Analysing body fluids, such as blood and urine, for different analytes plays an important role in clinical diagnosis, wherein a continued challenge lies in providing precise parameters and reliable quantitative results on ever smaller sample volumes as rapidly as possible. Providing timely measurement results on very small sample volumes is particularly important in the context of intensive care clinical diagnostics, not the least in neonatal care, which may require a sampling frequency of 15-20 per day in order to provide an adequate monitoring of a patient. Parameters of body fluids that are frequently monitored include concentrations of electrolytes and metabolites in a blood sample, as well as the haematocrit value of the blood sample. For example, measuring $pCO_2$, $pO_2$, pH, $Na^+$, $K^+$, $Ca^{2+}$, $Cl^-$, glucose, lactate and haemoglobin values are primary clinical indications in assessing the condition of a medical patient. A number of different analysers currently exist for making such multiple parameter measurements, wherein some designs make use of miniaturized measurement chambers and sensor cartridges aimed at reducing the sample amount required, yet meeting the physical limitations imposed by e.g. sensor design, geometries and wiring. For example, U.S. Pat. No. 5,916,425, discloses an electronic wiring substrate for sensors formed over a sub-miniature through hole. A relative large number of sensors can be formed on the surface of the substrate within a relative small fluid flow cell. U.S. Pat. No. 6,123,820 discloses sensor cartridges including a fluid constituent-selective sensor membrane in direct sealing contact with a face of a flow-through sample cell in surrounding relationship to a sensor port. The sensor cartridge includes a flow-through sample cell having a zig-zag or serpentine flow channel so as to provide a series of sensor ports on both of the opposed cell faces. However, this type of cartridge is complex to produce. Furthermore, the flow geometry of this sensor cartridge is particularly complex, which makes this type of sensor cartridges prone to the accumulation of contamination in the individual sample chambers. An advantageous alternative to these approaches is disclosed in U.S. Pat. No. 8,728,288, which relates to a sensor assembly for body fluids. The sensor assembly of U.S. Pat. No. 8,728,288 comprises: a first electronic wiring substrate having a first and a second surface and at least one analyte sensor formed on the first surface thereof, the at least one analyte sensor being connected with one or more electrical contact points; a second electronic wiring substrate having a first and a second surface and at least one analyte sensor formed on the first surface part thereof, the at least one analyte sensor being connected with one or more electrical contact points, and a spacer having a through-going recess with a first and a second opening; wherein the first substrate, the second substrate and the spacer are arranged in a layered structure, where the first surface of the first substrate closes the first opening of the spacer and the first surface of the second substrate closes the second opening of the spacer, thereby forming a measuring cell which is faced by at least one sensor from each of the substrates. Using the measuring cell of U.S. Pat. No. 8,728,288 it is possible to measure two or more parameters in the same measuring cell, without any significant interference between opposing analyte sensors, although no walls, channels or the like are present to keep the analyte sensors separated. In most cases the analyte sensors on opposing surfaces in the measuring cell may be placed facing each other or offset to each other as desired. The measuring cell of the sensor assembly may be faced by at least two or more sensors from one of the substrates or from each of the substrates. Typically, the measuring cell is elongated with a series of sensor surfaces formed on at least one of the substrates and arranged sequentially along the measurement cell. The measuring cell facilitates to measure a large number of parameter values on a very small sample.

Particular challenges arise in the above-mentioned flow or measuring cells for multiple parameter measurements on very small sample volumes when designing the cells for multiple uses, since this requires reliably filling, emptying, and re-filling such cells with liquid samples in a consistently repeatable manner. Such challenges may include problems of properly wetting all sensor surfaces during filling so as to ensure correct interaction between the sensor and the sample to ensure correct quantitative measurement results, problems of liquid of a first charge of a liquid sample remaining in the cell and thus contaminating a subsequent charge of another liquid sample, or problems of bubble formation and liquid entrapment in the cell. The same challenges do not arise in the same way in a disposable measuring cell for single-use, which is only filled one time with a liquid sample, and discarded after measurements have been obtained.

Therefore there is a need for a reusable device for reliably measuring multiple different parameters on body fluids, which is adapted for measuring on very small sample volumes, and which allows for reliable filling, emptying, and re-filling the device with liquid samples. In particular, there is a need for such a device that is adapted for use with body fluids, such as blood or urine.

According to one aspect, an object of the present invention is therefore to provide an improved reusable measurement device for analysing liquid samples of bodily fluids overcoming at least some of the drawbacks of the prior art, or at least to provide an alternative to prior art devices.

SUMMARY OF THE INVENTION

According to some embodiments, the object of the invention is achieved by a sensor assembly for body fluids as defined in claim 1, wherein further advantageous embodiments are defined in the dependent claims and the description below.

In a first aspect, a multiple-use sensor assembly for body fluids comprises:

- a measurement chamber extending in an axial direction from an inlet to an outlet, the measurement chamber having a transverse cross-section with side walls defining a chamber width in a horizontal direction, and with top and bottom walls defining a chamber height in a vertical direction, each of the side walls, top wall and bottom wall having a respective wall wettability for aqueous solutions;
- a first sensor adapted to measure a first parameter of body fluids, the first sensor having a first sensor surface exposed to the inside of the measurement chamber at a first axial position, the first sensor surface having a first wettability for aqueous solutions; and
- a second sensor adapted to measure a second parameter of body fluids, the second sensor having a second sensor surface exposed to the inside of the measurement chamber at a second axial position upstream or downstream from the first axial position, the second sensor surface having a second wettability for aqueous solutions higher than the first wettability;

wherein at the second axial position the chamber width exceeds the width of the second sensor surface, and wherein the measurement chamber at the second axial position has a widening in a horizontal direction as compared to the first axial position.

The sensor assembly is for analysing body fluids, which are aqueous solutions. The sensor assembly is furthermore for multiple-use. When used herein, the term "multiple-use sensor assembly" is intended to mean a sensor assembly that is adapted for being mounted in an analyser apparatus over an extended period of time, typically many days, weeks or even months, and used for analysis several times. During the lifetime of the sensor assembly it is intermittently washed with rinse solution and flushed with quality control and/or calibration solutions containing different concentrations of the analytically interesting ions and molecules according to a quality control/calibration schedule. This allows for determining proper calibration functions and for continually ensuring and documenting the quality of the measurement results.

The axial direction is along a principal direction of flow through the measurement chamber from the inlet to the outlet. Transverse directions are perpendicular to the axial direction, wherein the horizontal direction is a transverse direction from one side wall to the opposite side wall, and the vertical direction is a further transverse direction perpendicular to both the horizontal and axial directions, pointing from the bottom wall to the top wall.

Wetting is a consequence of intermolecular interactions at an interface between a liquid and a solid when the two are brought in contact with each other. Wetting may be seen as the ability of the liquid to seek contact and cover the solid surface. Wetting thus refers to the intermolecular interaction of the three phases involved in the filling, emptying and re-filling of the measurement chamber: a first fluid, such as a gas; a second fluid, such as a liquid sample to be analysed or a rinsing solution; and solid surfaces defining the measurement chamber in which the measurement is to be performed.

The degree of wetting may be referred to as wettability. Wettability is determined by a force balance between adhesive and cohesive forces. Wettability of a solid surface for a given liquid on may be characterised by a corresponding contact angle, where high wettability refers to contact angles below or equal to 90 degrees, and low wettability refers to contact angles above 90 degrees. A higher wettability for a given liquid corresponds to smaller contact angle, and a lower wettability corresponds to larger contact angle. Since the contact angle is commonly measured within the medium for which the wettability is determined, the contact angle provides an inverse measure of the wettability, i.e. a small contact angle indicates high wettability and a large contact angle indicates a low wettability. A solid surface having a higher wettability for a given liquid as compared to another solid surface thus means that the given liquid will exhibit a smaller contact angle on the former as compared to the latter. In another approach, the wettability of one solid surface, for a given liquid, may be compared to the wettability of another solid surface, for the same given liquid, in terms of a respective surface energy of the solid surfaces.

In general a measurement chamber is a chamber in which a sample is kept during measurement on the sample. A measurement chamber has on at least one inner surface at least one opening for bringing the sample into contact with the sensor surface of an analyte sensor. In a sensor assembly for measuring multiple parameters on the same sample of a body fluid, a plurality of different sensors is provided. The different sensors each have a sensor surface, which is typically configured for a specific analyte. The sensor surfaces are exposed to the inside of the measurement chamber for a liquid sample under analysis to contact the sensor surfaces and interact with the associated sensors so as to provide a parameter measurement for the respective analytes. The different sensor surfaces typically have different surface characteristics, including different wetting properties, as compared to each other, and as compared to the surfaces of the walls defining the measurement chamber.

As mentioned, the sensor assembly is for multiple-use. Multiple-use requires filling the measurement chamber with a liquid sample, emptying or equivalently purging out the liquid sample, and re-filling the measurement chamber with a subsequent liquid sample. Furthermore, the sensor assembly is for small sample volumes. Small sample volumes are desirable to reduce the consumption of bio-fluids, which can be particularly significant if a patient is to be monitored continually and sample material is scarce. As a result, the measurement chamber dimensions are reduced, which in turn results in an increasing significance of the wetting properties of the inner surfaces for the filling, emptying/purging, and re-filling performance of the measurement chamber. To successfully perform all these filling, emptying/purging, and re-filling steps under the additional constraints of small chamber dimensions, it has turned out that materials exhibiting a more or less neutral wetting for aqueous solutions are advantageous, e.g. surfaces with a wettability characterised by a contact angle for water in air close to 90 degrees, or at least materials exhibiting similar wetting properties are desirable. At the same time a simple geometry is highly advisable, since complex chamber geometry, under the additional constraints of small chamber dimensions, will cause and amplify many of the above-mentioned problems of filling, emptying/purging and re-filling the measurement chamber.

This balance may for certain analytes be achieved as a compromise by carefully selecting a surface material for the chamber walls that is compatible with the sensor surface materials employed, such as using encapsulants e.g. glass, metal, mineral such as kaolin, a polymer encapsulant or any combination thereof for the walls, and providing a straight-walled channel with a carefully selected constant channel width. Examples, for first sensors for which such a compromise may be found, include sensors for measuring any of the following parameters of body fluids: concentrations of electrolytes and metabolites in a body fluid sample, such as in a blood sample, as well as the haematocrit value of a blood sample. Preferably according to some embodiments, the first sensors are adapted to measure parameters selected from the group of $pCO_2$, $pO_2$, pH, and concentrations of $Na^+$, $K^+$, $Ca^{2+}$, $Cl^-$, glucose, lactate and haemoglobin. Advantageously, at least some of the one or more first sensors are solid state electrochemical sensors capped with an ion-selective membrane exposed to the inside of the measurement chamber. Advantageously according to some embodiments, a sensor assembly for body fluids comprises a plurality of first sensors which are all arranged in a straight-walled section of the measurement chamber, wherein each of the first sensors has a respective first axial position.

An important achievement of the present invention is that it embraces the particular case where the above compromise is not easily found—if at all possible. Such a case may arise, for example, if a particular set of first analyte sensors adapted for measuring a corresponding set of respective first parameters needs to be supplemented with a second sensor for a particular analyte, which requires a particular second sensor surface that has significantly different wetting properties as compared to any of the surfaces of the first sensors, and in particular a second sensor surface with a significantly higher wettability for aqueous solutions as compared to the first sensor surfaces. An example for a second sensor surface with significantly different wettability properties is a membrane made of a material that swells due to absorption of water in the membrane when exposed to a liquid sample of an aqueous solution.

The significantly different wettability properties of such a second sensor surface may destabilize a flow-front and may thus affect the reliability of the filling, emptying/purging, and re-filling performance of the sensor assembly. The problem is resolved by providing a widening around the second sensor surface with a width of the measurement chamber at the widening that exceeds the width of the second sensor surface, thereby allowing for counteracting a flow-front destabilization by the second sensor surface.

Advantageously, a transverse dimension of the measurement chamber at the second axial position and in a direction parallel to the second sensor surface exceeds a transverse dimension of the second sensor surface in the same direction. Advantageously a ratio of chamber width over sensor surface width at the second axial position is in the range 1.2-3.6, or in the range 1.4-2.8, or in the range 1.5-2.4.

Preferably according to some embodiments, the sensor surfaces are parallel to a horizontal plane spanned by the horizontal and axial directions. Preferably according to some embodiments, the sensor surfaces are arranged in a horizontal wall, such as in the top wall or in the bottom wall. Thereby a relatively smooth-walled and sealed inner surface is obtained, which is conducive for the flow performance of the measurement chamber. Further according to some embodiments, sensor surfaces are arranged both in the top wall and in the bottom wall. Thereby a compact sensor arrangement is achieved allowing for a large number of simultaneous analyte measurements being performed on a small sample volume.

In a practical approach for adapting the geometry of the widening, the skilled person may advantageously visualize the relative wettability of different parts of the inner surfaces of the measurement chamber, e.g. by recording a flow-front propagation during representative filling, emptying/purging and/or re-filling sequences with a high speed camera and observing the dynamic wetting behaviour during these sequences. The observations readily allow for a systematic optimization of the detailed geometry of the widening and its arrangement with respect to the second sensor surface. For example, a swelling membrane as the one mentioned above, which is deployed as a second sensor surface, may be perceived as highly hydrophilic as compared to remaining surfaces in the measurement chamber, including wall and first sensor surfaces, and a flow-front stabilizing widening around the second sensor surface may be devised accordingly, based on flow-front visualization data.

Further according to some embodiments of the sensor assembly, the second wettability for aqueous solutions of the second sensor surface is higher than the wall wettability for aqueous solutions. Thereby, the wall wettability may be selected or adapted to match the wettability range of the first sensor surfaces.

Further according to some embodiments of the sensor assembly, the second sensor is in a horizontal direction arranged centrally in the measurement chamber. Preferably, the first and second sensor surfaces are arranged parallel with a horizontal wall, such as the top wall and/or the bottom wall of the measurement chamber.

The second sensor surface and the measurement chamber at the second axial position are dimensioned such that the width of the measurement chamber is larger than the width of the sensor. When the second sensor in a horizontal direction is arranged centrally in the measurement chamber with respect to the side walls, parallel flow paths are provided around the second sensor surface. The parallel flow paths bypass the second sensor surface on either side thereof, as seen in the horizontal direction. The parallel flow paths have surfaces that may both be characterised by the same wall wettability, which may be significantly different from the second wettability characterising the second sensor surface. By providing flow paths with the same, well-defined wetting properties on either side of the second sensor surface, the wetting behaviour of a flow-front passing in an axial direction through the widening is effectively "pinned" on either side of the second sensor surface. This pinning of the wettability has a stabilizing effect on the flow-front as it passes through the measurement chamber, where the flow-front is allowed to deform in a horizontally central portion of the measurement chamber, all the while the flow front at the edges along the side walls keep up with each other travelling along the axial direction at the same speed.

It may be noted that the term "flow-front" as used herein refers to a fluid interface extending transversely across the measurement chamber and travelling along a generally axial direction from the inlet to the outlet, wherein the fluid interface separates a first fluid, such as a gas, from a second fluid, such as a liquid sample to be analysed or a rinsing solution. In a filling step, the first fluid precedes the second fluid, i.e. the measurement chamber is filled with the second fluid replacing the first. In an emptying step, the first fluid follows the second fluid, i.e. the measurement chamber is filled with the first fluid replacing the second.

Advantageously according to some embodiments of the sensor assembly, a ratio of the chamber width over the sensor width is larger at the second axial position than at the first axial position. Accordingly, the parallel flow paths bypassing the second sensor surface are more prominent, and may therefore enhance the contribution of the wall wettability to stabilizing the flow front at the second axial position as compared to the first axial position. This is particularly advantageous in the case, where the wettability of the second sensor surface differs significantly from both the first sensor surfaces and the wall material, whereas the variations in wettability of the first sensor surfaces and the wall material are less pronounced.

Further according to some embodiments of the sensor assembly, the measurement chamber is symmetric with respect to an axially oriented axis of symmetry as seen in a vertical projection. Thereby a symmetric flow front fluid interface is achieved between a first fluid, typically a gas, and a second fluid, e.g. a liquid sample, to be filled into, emptied out from, or re-filled into the chamber. The liquid sample may be e.g. a sample of a body fluid to be measured, a sample of a rinse liquid, a sample of a quality control liquid, or a sample of a calibration liquid. The symmetry strongly contributes to an improved stability of the flow front in the measurement chamber as it passes from the inlet to the outlet. An improved stability of the flow front refers to a reduced tendency of the flow front to break up to form bubbles/droplets that are then left behind in the measurement chamber, thereby impairing the filling, emptying, purging or re-filling operation.

A vertical projection as used herein is understood as a projection in a vertical direction onto a horizontal plane spanned by the axial and horizontal directions. In the present context of symmetry with respect to an axially oriented surface, this corresponds to the measurement chamber as seen in a horizontal direction being symmetric with respect to a mirror plane spanned by the axial and vertical directions.

Preferably, the second sensor surface is also shaped and arranged symmetrically with respect to the axis of symmetry of the measurement chamber within the widening. Such a symmetric arrangement of the second sensor further contributes to an improved stability of the flow front. Further preferably, the first sensor surfaces are arranged along the axis of symmetry of the measurement chamber. Yet further preferably, the first sensor surfaces are also symmetric with respect to the axis of symmetry of the measurement chamber. Such symmetric arrangements of the first and/or second sensors further contribute to an improved stability of the flow front.

As mentioned above, the measurement chamber is in a vertical direction defined by top and bottom walls spaced apart from each other by the chamber height and in a horizontal direction by side walls spaced apart from each other by the chamber width. Each of the walls may have respective wall wettability for aqueous solutions. Typically, the top and bottom walls have the same or very similar surface materials exposed to the inside of the measurement chamber, e.g. a polymethylmethacrylat (PMMA) or polyethylmethacrylate (PEM) based polymer encapsulant, and side walls made of different materials, such as a spacer gasket made of a polyethylene terephthalate (PET) carrier, with an adhesive on either side thereof. After priming of the pristine chamber walls during a first filling, the side walls and/or corners where the sidewalls intersect the top and bottom walls tend to retain a surface film of water resulting in an enhanced edge wetting when re-filling.

Preferably, the measurement chamber has a simple geometry, such as a straight channel comprising at least two sensor surfaces integrated in the walls. Typically, the measurement chamber is shaped as a generally straight channel with parallel walls. An advantage of a simple geometry is improved filling and re-filling performance of the measurement chamber, and thus a more stable and reliable operation of the sensor assembly than for a more complex measurement chamber geometry. Preferably, the walls defining the flow channel have a soft-shaped geometry avoiding sharp edges, projections, or otherwise sudden changes of the flow channel dimensions. Thereby, the risk of bubble entrapment during filling and re-filling steps is reduced.

Further according to some embodiments of the sensor assembly, the measurement chamber as seen in a vertical projection comprises a first section with axially extending straight side walls and a second section with curved side walls forming the widening around the second sensor surface at the second axial position. Advantageously, the widening is formed by concave sections of the sidewalls bulging outward as seen from the inside of the measurement chamber. Preferably, the curved sidewalls forming the widening are bulging symmetrically outward from the side walls of the straight section. Thereby, a smooth, and preferably symmetric, widening is provided. Such a shape of the widening is may easily be defined in a layered assembly construction by accordingly adapting a contour of a through-going recess in the spacer gasket defining the layout of the measurement chamber.

Further according to some embodiments of the sensor assembly, the top and bottom walls are plane parallel and separated from each other by a spacer gasket with a through-going recess defining a contour of the measurement chamber as seen in a vertical projection, wherein the spacer gasket has a thickness determining the chamber height. The present invention is particularly useful as an improvement to the filling, emptying/purging, and re-filling performance of sensor assemblies with a flat-shaped channel cross-section, such as the ones discussed and disclosed in U.S. Pat. No. 8,728, 288.

Advantageously according to some embodiments of a sensor assembly for body fluids, the chamber width exceeds the chamber height by a factor of at least two, at least three, at least four, or about five. Further advantageously, an upper limit of the factor by which the chamber width exceeds the chamber height is six, or eight, or ten.

Due to geometric limitations on the sensor surface dimensions, a width of the above-mentioned flow or measuring cells for small sample volumes is typically larger than a height of the cells. A cross-section of the flow or measuring cells therefore typically has a flat and wide cross-section, shaped like a letter slit, as seen in an axial direction along a flow direction through the measurement cell from an inlet at one end to an outlet at an opposite end thereof. Typical dimensions for such flow and measuring cells may be in the range of millimetres for the width, and in a submillimetre-range, such as a few hundred micrometres, for the height. While these cell geometries and dimensions may ensure a good usage of the sample, it poses at the same time a challenge to the filling, emptying and re-filling of the measurement chamber Further according to some embodiments of the sensor assembly, a chamber height is within the range 100 µm-1 mm, 200 µm-800 µm, or 300 µm-600 µm.

Further according to some embodiments of the sensor assembly, a chamber width is within the range 1 mm-10 mm, 1.5 mm-7 mm, 2 mm-4 mm.

The measurement chamber is dimensioned at an intermediate scale between a macroscale where flow phenomena are dominated by external driving forces applied to the fluid channel, such as pressure and gravity driven flow, on the one hand, and a microscale where microfluidic flow phenomena prevail that are dominated by microscopic forces, such as capillary interactions between the flow channel walls and the fluid. In flow channels that have dimensions in the intermediate scale both macroscopic and microscopic flow phenomena are of comparable importance for the filling, emptying, and re-filling behaviour of a measurement chamber of such dimensions.

Further according to some embodiments of the sensor assembly, the measurement chamber further comprises a flow shaping surface element arranged in a wall of the measurement chamber at a third axial position downstream of the widening and adjacent thereto, the flow shaping surface element having a surface element wettability for aqueous solutions different from a wall wettability of surrounding wall surface material. The flow shaping element presents an area of modified wettability, and thus of modified fluid-solid interaction to a fluid flowing through the measurement chamber. The modified interaction influences the propagation of a flow-front fluid interface through the measurement chamber. The interface interaction, which may be configured to vary in a transverse direction across the measurement chamber, may thus be employed to shape the flow front, e.g. in order to compensate for an axial deformation of the flow front.

Further according to some embodiments of the sensor assembly, the surface element wettability of the flow shaping surface element is lower than the respective top and bottom wall wettability for aqueous solutions.

Further according to some embodiments of the sensor assembly, the flow shaping surface element is made of or comprising metal, such as gold, palladium, silver or platin, or any combination thereof, or any material having a lower wettability property as compared with the foregoing surface. Providing a metal surface allows for providing a pronounced fluid-solid interface interaction induced drag for an efficient flow shaping of a flow front passing the flow shaping surface element. Alternatively the flow shaping surface elements is a sensor, such as $pCO_2$, $pO_2$ or Cl sensor.

Further according to some embodiments of the sensor assembly, an upstream edge of the flow shaping surface element is convex as seen in an axial direction from the inlet to the outlet. Thereby an improved flow front re-shaping that compensates for flow front deformations after the second sensor surface is achieved. The convex shape is particularly useful for reliable filling of the measurement chamber with a liquid replacing a gas.

Further according to some embodiments of the sensor assembly, a downstream edge of the flow shaping surface element is concave as seen in an axial direction from the inlet to the outlet. Thereby an improved flow front re-shaping that compensates for flow front deformations after the second sensor surface is achieved. The concave shape on a downstream side of the flow element is particularly useful for reliable emptying of the measurement chamber, i.e. filling the measurement chamber with a gas replacing a liquid.

Advantageously according to some embodiments, the flow shaping surface element has a circular, elliptical, polygonal, or similar contour, such as a contour comprising curved arc-sections. Advantageously, the layout of the flow shaping surface element has a regular contour, preferably at least symmetric with respect to an axially oriented symmetry axis. Preferably, the flow shaping surface element is arranged on the same wall as the second sensor surface. Furthermore an arrangement of a plurality of flow shaping surface elements may be conceived. The flow shaping surface element or part of the flow shaping element may thus be located on the same wall, the opposite wall or the side wall.

Advantageously according to some embodiments, the surface element has a width that is less than the width of the channel at the axial position of the flow shaping surface element. Further advantageously, the flow shaping surface element is arranged centrally, preferably symmetrically with respect to the side walls of the measurement chamber as seen in a horizontal direction.

Further according to some embodiments of the sensor assembly, the second sensor is a solid state electrochemical sensor capped with an ion-selective membrane, wherein an uppermost layer forming the second sensor surface comprises an enzyme and a binder-polymer. Advantageously, the solid state sensor has a membrane forming the sensor surface exposed to the inside of the measurement chamber, wherein the membrane is selectively transmissible for a specific ion. The membrane material may have particular wetting properties as governed by the combination of the binder polymer and the enzyme.

Further according to preferred embodiments of the sensor assembly, the enzyme is urease and the binder polymer is a polyurethane or polyurethane-based. A sensor with this capping membrane is useful for detecting/measuring urea in a sample of a body fluid.

Further according to some embodiments of the sensor assembly, the second sensor is a urea sensor. By providing an urea sensor in combination with a plurality of first sensors adapted to measure a set of bio-analytical parameters, such as those mentioned previously, a particularly useful diagnostic landscape of a relatively small sample of a body fluid can be rapidly mapped, wherein the particular shape of the measurement chamber comprising a widening at the urea sensor ensures a particularly consistent and reliable filling, emptying/purging and re-filling performance.

BRIEF DESCRIPTION OF THE DRAWINGS

Preferred embodiments of the invention will be described in more detail in connection with the appended drawings, which show in FIG. 1 a sensor assembly according to one embodiment in a vertical projection, FIG. 2 a transverse cross-sectional view along line II-II of the sensor assembly of FIG. 1, FIG. 3 a filling sequence for the sensor assembly of FIG. 1, FIG. 4 a filling sequence for a sensor assembly with a measurement chamber shaped according to the prior art, FIG. 5 an emptying sequence for the sensor assembly of FIG. 1, and in FIG. 6 an emptying sequence for the sensor assembly with a prior art measurement chamber of FIG. 4.

DETAILED DESCRIPTION OF PREFERRED EMBODIMENTS

Figure 3:
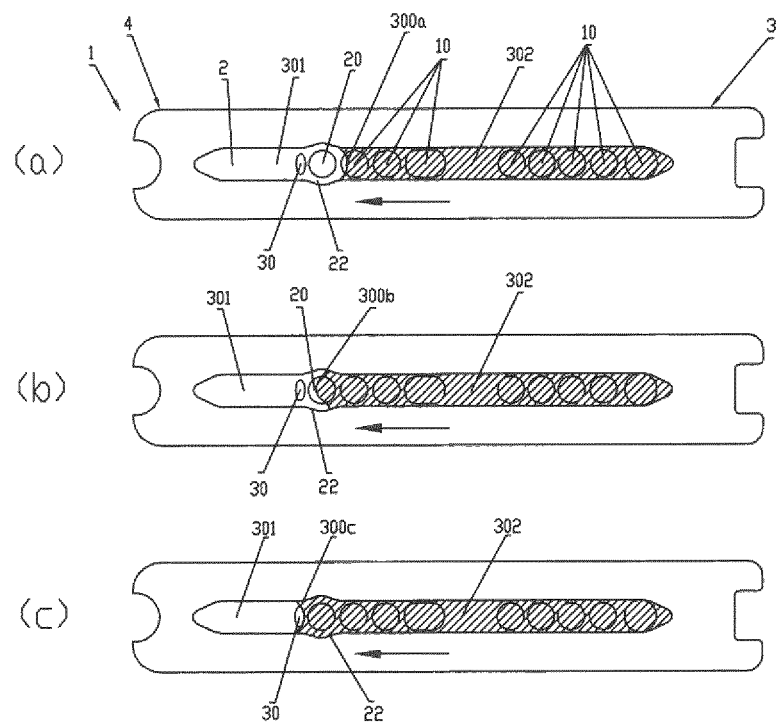

FIG. 1 shows a top elevation view of a sensor assembly 1 adapted for measuring a number of different parameters on a body fluid. The sensor array has a measuring chamber 2 defining a flow channel for fluid flow from an inlet at an inlet end 3 to an outlet at an outlet end 4 of the sensor assembly 1. The measurement chamber 2 has axially extending side walls 5, 6 defining a chamber width of the measurement chamber 2 in a horizontal direction, and a bottom wall 7 and top wall 8 (made transparent in the view of FIG. 1) defining a chamber height of the measurement chamber 2 in a vertical direction. The measurement chamber 2 is formed as a generally straight-walled flow channel that is elongated in the axial direction from the inlet end 3 to the outlet end 4, wherein the straight-walled sections of the side walls 5, 6 are parallel to the axial direction. The measurement chamber 2 has a widening 22 formed by curved side wall sections 23, 24 bulging outward as seen from the inside of the measurement chamber 2. The layout of the measurement chamber as seen in a vertical projection (top elevation) is symmetric with respect to an axially oriented centre axis S.

A transverse cross-section of the measurement chamber 2 along line II-II is best seen in FIG. 2. The top and bottom walls 7, 8 may be carried by ceramic wiring substrates C, which towards the inside of the measurement chamber 2 are covered by encapsulants e.g. glass, metal, mineral such as kaolin, a polymer encapsulant or any combination thereof A. The side walls 5, 6 are defined by a spacer gasket B, wherein the thickness of the spacer gasket B in a vertical direction determines the height of the measurement chamber 2. The layout of the measurement chamber 2 including the straight walled section and the widening 22 is defined as the contour of a through-going recess in the spacer gasket 9. Each of the side walls, top wall and bottom wall having a respective wall wettability for aqueous solutions as determined by the respective materials exposed to the inside of the measurement chamber. Typically, the top and bottom walls are coated with the same encapsulants e.g. glass, metal, mineral such as kaolin or a polymer encapsulant material, such as a polymethylmethacrylat (PMMA) or polyethylmethacrylate (PEM) based polymer encapsulant or any combination thereof. The spacer gasket may be of different materials, such as a polyethylene terephthalate (PET) carrier film, with an adhesive on either side thereof. Accordingly, the top, bottom and side walls have a respective wall wettability of the top and bottom wall encapsulant materials, and side wall wettability determined by the spacer gasket material—or by a wetting water film covering the spacer gasket material after priming of the chamber.

The sensor assembly comprises a sequence of first sensors 10a-h lined up in the axial direction at respective first axial positions along the length of the measurement chamber 2. The first sensors 10a-h have respective first sensor surfaces 11a-h exposed to the inside of the measurement chamber 2. The first sensor surfaces 11a-h are parallel to the bottom wall, and are both symmetrically shaped and symmetrically arranged with respect to the axially oriented centre axis S. The first sensor surfaces 11a-h each have a respective first wettability for aqueous solutions as determined by the respective outermost membrane material exposed to the chamber volume. The respective first wettability may differ from sensor type to sensor type depending on the particular material of the outermost membrane exposed to the chamber volume. The respective first sensor may in each case also differ from the wettability of the walls surrounding it. However, the first sensor wettability and the wall wettability are typically comparable to each other. Preferably, the first sensor surfaces and/or the wall surfaces exposed to the chamber volume are slightly hydrophilic, close to neutral wetting, for good performance for both filling and emptying of the measurement chamber. In particular a good emptying performance turns out to be rather crucial for a stable operation of the sample assembly as a multiple-use device.

The sensor assembly 1 further comprises a second sensor 20 at a second axial position downstream of the first sensors. The second sensor 20 has a second sensor surface 21 with a second wettability for aqueous solutions. The second sensors 20 differ from the first sensors in that the sensor surface 21 of the second sensor 20 exposed to the inside of the measurement chamber 2 has a significantly higher wettability than the surfaces 11a-h of the first sensors 10a-h, thus strongly affecting the filling and emptying behaviour of the measurement chamber as further discussed below with respect to FIGS. 3-6. The significantly higher wettability results in an enhanced tendency to perturb interfaces between a first fluid, such as a gas, and a second fluid, such as a liquid sample of a body fluid or a similar aqueous solution, as the interface travels as a flow front along the measurement chamber 2 and passes the second sensor surface 21. The widening 22 formed by the concavely outward bulging curved side wall sections 23, 24 acts to stabilize the flow fronts as they pass the second axial position by offering parallel flow passages on either side around the second sensor surface 21. The surfaces of the parallel flow passages exposed to the measurement chamber 2 have wettability properties corresponding to the remaining portions of the chamber 2, with a wall wettability of the top and bottom wall encapsulant materials, and with a side wall wettability determined by the spacer gasket material—or by a wetting water film covering the spacer gasket material after priming of the chamber.

The sensor assembly 1 further comprises a flow shaping surface element 30 with a surface 31 facing the inside of the measurement chamber at a third axial position downstream of the second axial position. The flow shaping surface element 30 is arranged on the bottom wall 7 with its surface 31 parallel thereto. The exposed surface 31 of the flow shaping surface element 30 is made of or comprising a metal, such as gold, palladium, silver, platin, or any combination thereof, or any material having a lower wettability property as compared with the foregoing surface and has a surface element wettability that is lower than the wall wettability of the surrounding bottom wall surfaces.

Actual contact angles for fluids in contact with the various different solid surfaces making up the inside of the measurement chamber 2 are difficult to define and measure within the confined geometry of a small flow channel, such as typical intermediate scale measurement chambers for body fluids that have dimensions in a regime between a macroscale and a microscale. The different wetting behaviour of the different surfaces and their significance for the filling and emptying behaviour may, however, be visualized and recorded using high speed vision technologies, so as to observe the dynamic filling and emptying performance of a specific channel. This is by way of example described in the following. Example 1 describes details of materials and dimensions for a sensor assembly according to one embodiment with reference to the layout as shown in FIGS. 1 and 2. Example 2 provides visualization data obtained on a sensor assembly according to Example 1 having a widening 22 as shown in FIG. 1 as compared to a prior art layout without such a widening in the measurement chamber.

Example 1

Referring in the following to the embodiment shown in FIGS. 1 and 2 and described above, a non-limiting example for an advantageous choice of materials and dimensions for a sensor assembly 1 is given. The sensor assembly 1 has top and bottom walls 7, 8 made of a 0.7 mm thick ceramics substrate C covered by a polymer encapsulant A, such as a polymethylmethacrylat (PMMA) or polyethylmethacrylate (PEM) based polymer. The top and bottom walls 7, 8 are separated by the spacer gasket B made of a 250 µm thick polyethylene terephthalate (PET) carrier, with a 75 µm rubber based thermoplastic adhesive on either side thereof, resulting in a chamber height of 400 µm±20 µm. The through-going recess defining the layout of the measurement chamber 2 has in an axial direction a length of 34 mm, and in a horizontal direction perpendicular to the axial direction a constant width of 2.3 mm in the region of the straight-walled sections. A circular widening of diameter 3 mm is formed symmetrically over the straight channel at an axial position 9.1 mm from the downstream end of the measurement chamber, concentric with a location of the second sensor on the bottom wall.

A sequence of first sensor locations may be occupied by the following first sensors 10a-h with corresponding first sensor surface materials 11a-h:

sensor 10a/surface 11a: $pO_2$ (optical)/rigid PVC window
sensor 10b/surface 11b: vacant/wall encapsulant
sensor 10c/surface 11c: $Ca^{2+}$/plasticized PVC
sensor 10d/surface 11d: $Cl^-$/epoxy
sensor 10e/surface 11e: pH/plasticized PVC
sensor 10f/surface 11f: $pC_2$/silicone
sensor 10g/surface 11g: $Na^+$/plasticized PVC
sensor 10h/surface 11h: $K^+$/plasticized PVC A second sensor 20 may be a urea sensor, such as disclosed e.g. in co-pending international patent application PCT/EP2016/080607, which is hereby incorporated by reference, in particular on page 14-15 and example 1 on page 16. In particular, the urea sensor may expose an enzyme layer as a second sensor surface 21 towards the measurement chamber that comprises an enzyme and a binder-polymer. In particular, the enzyme is urease and the binder polymer is a polyurethane based polymer. More particularly, the enzyme component and the polyurethane based binder polymer are present at about 50% each. When exposed to an aqueous solution, the polyurethane based binder polymer matrix absorbs approximately 100% of water leading to a considerable swelling of the membrane layer forming the second sensor surface.

A flow shaping surface element 30 may be made of gold or a gold alloy.

Example 2

Referring to FIGS. 3-6 in the following, visualization data of a comparative study is illustrated as sequences taken from high speed video recordings of the filling and emptying of two sensor assemblies 1 with different measurement chambers 2, where corresponding features of the different measurement chambers 2 are denoted with the same reference numerals. The measurement chamber 2 of the sensor assembly 1 shown in FIGS. 3 and 5 corresponds to the embodiment shown in FIG. 1 with the further specifications according to Example 1 and a widening 22 at the location of the second sensor 20. The sensor assembly shown in FIGS. 4 and 6 differs from the sensor assembly shown in FIGS. 3 and 5 only by the absence of any widening in the measurement chamber, and in particular by the absence of any widening around the second sensor 20. The layout of the measurement chamber of FIGS. 4 and 6 as a long parallel channel without any widening would correspond to the flow channel layout of a prior art sensor assembly. Otherwise, the sensor assemblies shown in FIGS. 3-6 are identical, including the presence of a second sensor 20 and an elliptic flow shaping surface element 30 downstream of the second sensor 20. In the following, "filling" refers to replacing a gas 301, 401 in the respective measurement chamber 2 by feeding an aqueous solution 302, 402, which mimics a body fluid sample, to the measurement chamber 2 from the inlet end 3, and "emptying" refers to replacing the aqueous solution 502, 602 again by gas 501, 601 injected from the inlet end 3. In all four figures FIGS. 3-6 the flow direction is from the inlet end 3 on the right to the outlet end 4 on the left as also indicated by the arrows on each frame (a)-(c). The measurement chambers were all primed with an aqueous solution prior to the recorded sequences shown in FIGS. 3-6. The spacer gasket material of the side walls is therefore considered to be completely wet by a very thin aqueous film.

High speed recordings of the filling where taken using an EoSens 3CL MC3011 high speed camera with a CMOS image sensor available from Mikrotron GmbH, Germany using an image acquisition software kit (MBDirector KIT 2) with typical settings of the recording parameters set to a shutter time of 3500 µs, a frame rate of 285 frames per second at a frame size of 1200×122 pixels. It may be noted that flow rates are in the range of microliters per second (µl/s), wherein typical values are at least 20 µl/s for emptying and up to 65 µl/s for filling, and usually about 35 µl/s.

In the obtained high speed video recordings, the evolution of the shape of the respective flow fronts 300a-c, 400a-c, 500a-c, 600a-c is each time observed as the gas-liquid or liquid-gas interface travels along the measurement chamber, and in particular as the flow fronts 300a-c, 400a-c, 500a-c, 600a-c pass over the second sensor surface 21 of the second sensor 20 at the second axial position and over the surface 31 of the flow shaping surface element 30 at the third axial position downstream of the second axial position. In each of the FIGS. 3-6 three frames of the video recordings are selected where the flow fronts 300, 400, 500, 600 are at corresponding locations in the measurement chamber 2, namely (a) at the downstream end of the sequence of first sensors 10, just before reaching the second sensor 20; (b) at the second sensor 20; and (c) just downstream of the second sensor 20, at the flow shaping surface element 30. The selected video frames where then retraced as black and white line drawings, where the liquid phase each time is indicated as a hatched area.

FIG. 3 shows a filling sequence in a measurement chamber 2 with a widening 22 around the second sensor 20. In the first frame (a), a flow front 300a approaches the second sensor 20. The flow front 300a is concave as seen from the gas phase 301 towards the liquid phase 302. In the second frame (b), the flow front 300b has reached the second sensor 20 and has spread in a transverse direction over the widening 22. The flow front 300b is deformed due to the highly hydrophilic wetting behaviour of the surface of the centrally arranged second sensor 20. However, the centrally arranged second sensor 20 is surrounded by parallel flow passages of the widening bulges presenting a wetting behaviour to the liquid that corresponds to the wall wettability of the bottom wall encapsulant, which clearly is significantly lower than the wettability of the second sensor surface. A pronounced meniscus of liquid projecting in flow direction over the second sensor surface is observed, which is stabilised by the symmetrically arranged parallel flow passages of the widening 22 where the wetting behaviour is pinned to the bottom wall wettability. In the third frame (c), the flow front 300c has reached the upstream edge of a flow shaping surface element 30 having a wettability that is lower than the wall wettability of the surrounding bottom wall encapsulant. The surface interaction of the liquid with the flow shaping surface element slows down the propagation of the liquid in the centre as compared to the edge regions. As a consequence, the flow front 300c regains its concave shape as seen from the preceding gas phase 301 towards the trailing liquid phase 302.

Figure 4:
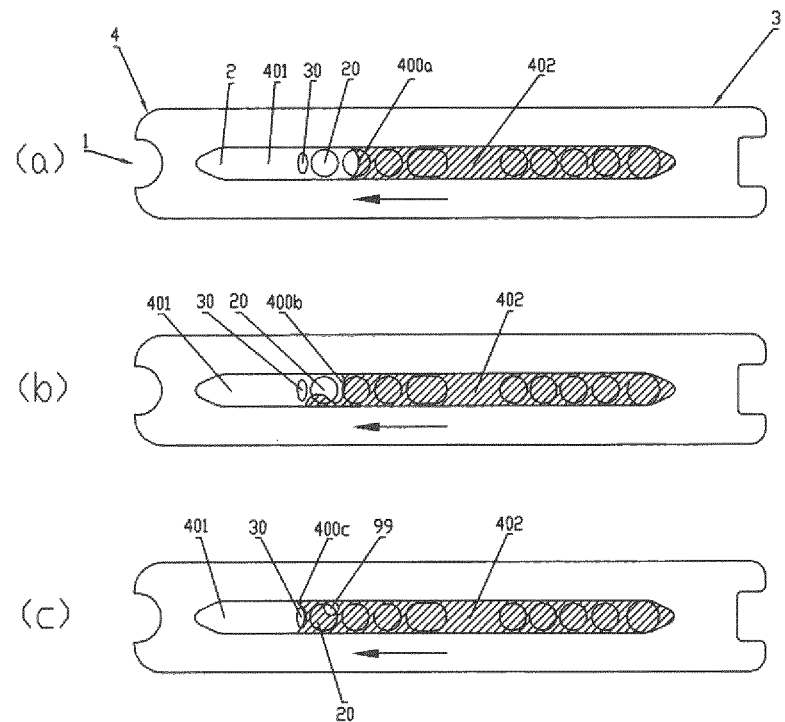

FIG. 4 shows a filling sequence in a measurement chamber 2 without any widening around the second sensor 20. In the first frame (a), a flow front 400a approaches the second sensor 20. The flow front 400a is concave as seen from the gas phase 401 towards the liquid phase 402. In the second frame (b), the flow front 400b has reached the second sensor 20. The flow front 400b has "tilted", due to the highly hydrophilic wetting behaviour of the surface of the second sensor 20 in combination with small variations in the side wall wettability. The flow front 400b is considered destabilized and exhibits a complex shape. In the third frame (c), the flow front 400c has reached the upstream edge of flow shaping surface element 30 having a wettability that is lower than the wall wettability of the surrounding bottom wall encapsulant. The surface interaction of the liquid with the flow shaping surface element slows down the propagation of the liquid in the centre as compared to the edge regions, and the flow front 400c regains its concave shape as seen from the preceding gas phase 401 towards the trailing liquid phase 402. However, as a consequence of the instability of the flow front 400b upon passing over the second sensor 20 a bubble 99 has been entrapped at the second sensor 20.

Figure 5:
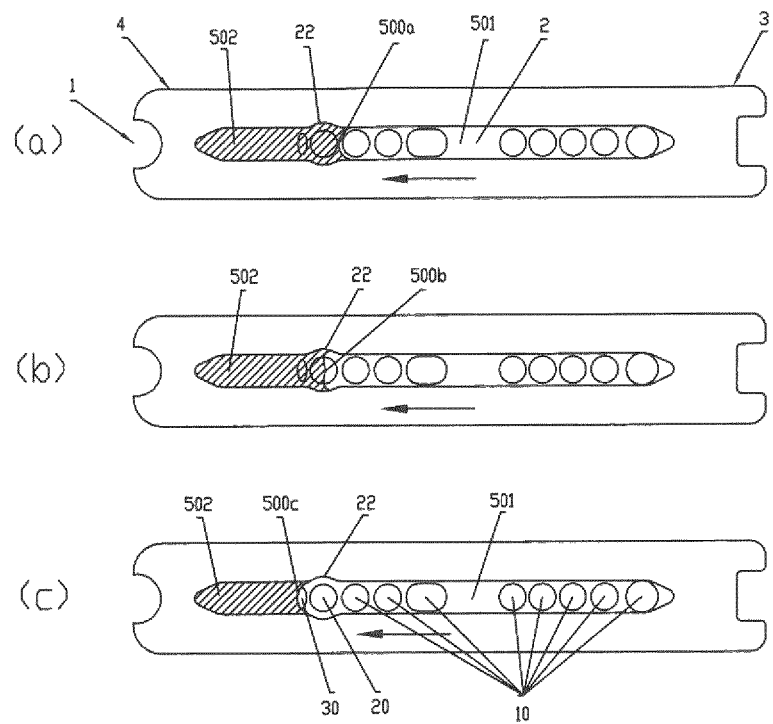

FIG. 5 shows an emptying sequence in a measurement chamber 2 with a widening 22 around the second sensor 20. In the first frame (a), a flow front 500a approaches the second sensor 20. The flow front 500a is concave as seen from the gas phase 501 towards the liquid phase 502. In the second frame (b), the flow front 500b has reached the second sensor 20 and has spread in a transverse direction over the widening 22. The flow front 500b is deformed due to the highly hydrophilic wetting behaviour of the surface of the centrally arranged second sensor 20. However, the centrally arranged second sensor 20 is surrounded by parallel flow passages of the widening bulges presenting a wetting behaviour to the liquid that corresponds to the wall wettability of the bottom wall encapsulant, which clearly is significantly lower than the wettability of the second sensor surface. A flattened profile is observed as the flow front 500b propagates over the second sensor 20, which is stabilised by the symmetrically arranged parallel flow passages of the widening 22 where the wetting behaviour is pinned to the bottom wall wettability. In the third frame (c), the flow front 500c has reached the downstream edge of a flow shaping surface element 30 having a wettability that is lower than the wall wettability of the surrounding bottom wall encapsulant. As the liquid phase 502 passes over the flow shaping surface element 30, the surface interaction of the liquid 502 with the flow shaping surface element 30 repels the liquid phase 502 towards regions with higher wettability. The downstream edge of the flow shaping surface element 30 is concave as seen in an axial direction from the inlet towards the outlet, i.e. as seen in the direction of flow. As a consequence, the flow front 500c regains its concave shape as seen from the trailing gas phase 501 towards the preceding liquid phase 502.

Figure 6:
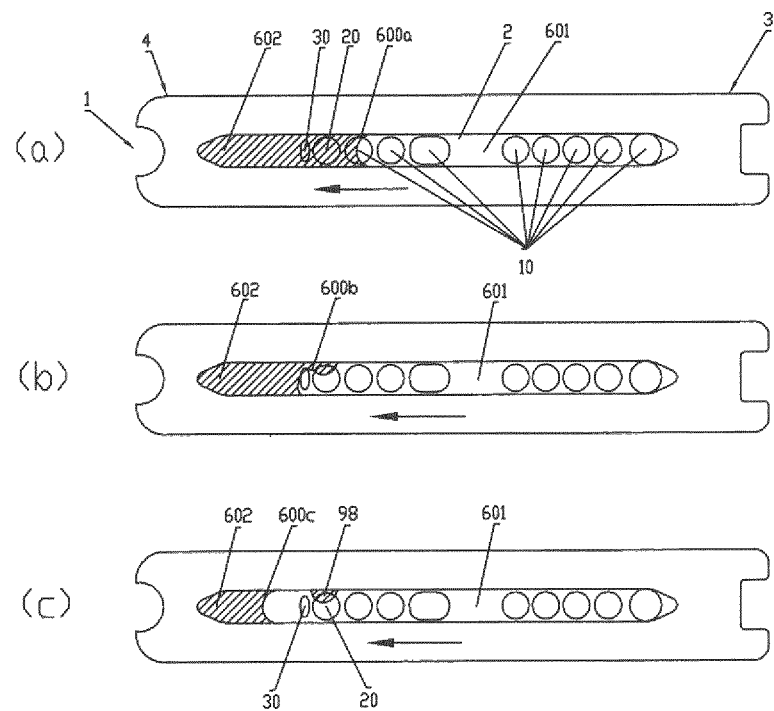

FIG. 6 shows an emptying sequence in a measurement chamber 2 without any widening around the second sensor 20. In the first frame (a), a flow front 600a approaches the second sensor 20. The flow front 600a is concave as seen from the trailing gas phase 601 towards the preceding liquid phase 602. In the second frame (b), the flow front 600b has reached the second sensor 20. The flow front 600b has "tilted", due to the highly hydrophilic wetting behaviour of the surface of the second sensor 20 in combination with small variations in the side wall wettability. The flow front 600b is considered destabilized and exhibits a complex shape. In the third frame (c), the flow front 600c has passed the flow shaping surface element 30 having a wettability that is lower than the wall wettability of the surrounding bottom wall encapsulant. As the liquid phase 602 passes over the flow shaping surface element 30, the surface interaction of the liquid 602 with the flow shaping surface element 30 repels the liquid phase 602 towards regions with higher wettability. The downstream edge of the flow shaping surface element 30 is concave as seen in an axial direction from the inlet towards the outlet, i.e. as seen in the direction of flow. As a consequence, the flow front 600c regains its concave shape as seen from the trailing gas phase 601 towards the preceding liquid phase 602. However, as a consequence of the instability of the flow front 600b upon passing over the second sensor 20 a droplet 98 remains at the second sensor 20.

The invention claimed is:

1. A sensor assembly for bio-analytic measurements in body fluids, the sensor assembly comprising:
    a measurement chamber extending in an axial direction from an inlet to an outlet, the measurement chamber having a transverse cross-section with side walls defining a chamber width in a horizontal direction, and with top and bottom walls defining a chamber height in a vertical direction, each of the side walls, top wall and bottom wall having a respective wall wettability for aqueous solutions;
    a first sensor configured to measure a first parameter of body fluids, the first sensor having a first sensor surface exposed to the inside of the measurement chamber at a first axial position, the first sensor surface having a first wettability for aqueous solutions; and
    a second sensor configured to measure a second parameter of body fluids, the second sensor having a second sensor surface exposed to the inside of the measurement chamber at a second axial position upstream or downstream from the first axial position, the second sensor surface having a second wettability for aqueous solutions higher than the first wettability.

2. The sensor assembly for bio-analytic measurements in body fluids according to claim 1, wherein the second wettability for aqueous solutions of the second sensor surface is higher than the wall wettability for aqueous solutions.

3. The sensor assembly for bio-analytic measurements in body fluids according to claim 1, wherein the second sensor is in a horizontal direction arranged centrally in the measurement chamber.

4. The sensor assembly for bio-analytic measurements in body fluids according to claim 1, wherein the measurement chamber is symmetric with respect to an axially oriented axis of symmetry as seen in a vertical projection.

5. The sensor assembly for bio-analytic measurements in body fluids according to claim 1, wherein the measurement chamber as seen in a vertical projection comprises:
    a first section with axially extending straight side walls; and
    a second section with curved side walls forming a widening around the second sensor surface at the second axial position.

6. The sensor assembly for bio-analytic measurements in body fluids according to claim 1, wherein the top and bottom walls are plane parallel and separated from each other by a spacer gasket with a through-going recess defining a contour of the measurement chamber as seen in a vertical projection, wherein the spacer gasket has a thickness determining the chamber height.

7. The sensor assembly for bio-analytic measurements in body fluids according to claim 1, wherein a chamber height is from 100 μm to 1 mm.

8. The sensor assembly for bio-analytic measurements in body fluids according to claim 1, wherein a chamber height is from 200 μm to 800 μm.

9. The sensor assembly for bio-analytic measurements in body fluids according to claim 1, wherein a chamber height is from 300 μm to 600 μm.

10. The sensor assembly for bio-analytic measurements in body fluids according to claim 1, wherein a chamber width is from 1 to 10 mm.

11. The sensor assembly for bio-analytic measurements in body fluids according to claim 1, wherein a chamber width is from 1.5 to 7 mm.

12. The sensor assembly for bio-analytic measurements in body fluids according to claim 1, wherein a chamber width is from 2 to 4 mm.

13. The sensor assembly for bio-analytic measurements in body fluids according to claim 1, wherein at the second axial position the chamber width exceeds the width of the second sensor surface, and wherein the measurement chamber at the second axial position has a widening in a horizontal direction as compared to the first axial position.

14. The sensor assembly for bio-analytic measurements in body fluids according to claim 13, wherein the measurement chamber further comprises a flow shaping surface element arranged in a wall of the measurement chamber at a third axial position downstream of the widening and adjacent thereto, the flow shaping surface element having a surface element wettability for aqueous solutions different from a wall wettability of surrounding wall surface material.

15. The sensor assembly for bio-analytic measurements in body fluids according to claim 14, wherein the surface element wettability of the flow shaping surface element is lower than the respective top and bottom wall wettability for aqueous solutions.

16. The sensor assembly for bio-analytic measurements in body fluids according to claim 14, wherein the flow shaping surface element comprises a metal, wherein the metal comprises gold, palladium, silver, platin, or combinations thereof.

17. The sensor assembly for bio-analytic measurements in body fluids according to claim 14, wherein an upstream edge of the flow shaping surface element is convex as seen in an axial direction from the inlet to the outlet.

18. The sensor assembly for bio-analytic measurements in body fluids according to claim 14, wherein a downstream edge of the flow shaping surface element is concave as seen in an axial direction from the inlet to the outlet.

19. The sensor assembly for bio-analytic measurements in body fluids according to claim 1, wherein the second sensor is a solid state electrochemical sensor capped with an ion-selective membrane, wherein an uppermost layer forming the second sensor surface comprises an enzyme and a binder-polymer.

20. The sensor assembly for bio-analytic measurements in body fluids according to claim 1, wherein the second sensor is a urea sensor.

* * * * *